US005097035A

United States Patent [19]

Desai et al.

[11] Patent Number: 5,097,035
[45] Date of Patent: Mar. 17, 1992

[54] MONOBASIC DISOBUTAMIDE DERIVATIVES

[75] Inventors: Bipinchandra N. Desai, Vernon Hills; Robert J. Chorvat, Arlington Heights; Kurt J. Rorig, Glenview, all of Ill.

[73] Assignee: G. D. Searle & Co., Chicago, Ill.

[21] Appl. No.: 465,627

[22] Filed: Jan. 19, 1990

Related U.S. Application Data

[63] Continuation of Ser. No. 286,588, Dec. 19, 1988, abandoned, which is a continuation of Ser. No. 889,431, Jul. 25, 1986, abandoned, which is a continuation of Ser. No. 628,933, Jul. 9, 1984, Pat. No. 4,639,524.

[51] Int. Cl.$^5$ .............................................. C07D 21/32
[52] U.S. Cl. .................................... 546/226; 548/540
[58] Field of Search ............... 546/226; 514/330, 821, 514/923; 548/540

[56] References Cited

U.S. PATENT DOCUMENTS

| 2,776,282 | 1/1957 | Cusic ........................ 544/169 |
| 3,310,555 | 3/1967 | Pesson ...................... 546/226 |
| 3,639,476 | 2/1972 | Eberle ....................... 548/540 |
| 3,998,965 | 12/1976 | Gittes et al. ............... 514/521 |
| 4,035,497 | 7/1977 | Gittes et al. ............. 514/237.5 |
| 4,107,205 | 8/1978 | Renbarger et al. ........ 546/237 |
| 4,153,797 | 5/1979 | Renbarger et al. ........ 546/237 |
| 4,217,306 | 8/1980 | Yonan ....................... 564/165 |

OTHER PUBLICATIONS

Yen et al., *J. Med. Chem,* "Compounds Related to 4-diisopropylamino-2-phenyl-2-(2-pyridyl) Gatyramide," 17, (11), pp. 1131-1135 (1974).
Yonan et al., *J. Med. Chem.*, "Synthesis and Antiarrgthmic Activity of α,α-Bis[(dialaylamino)alkyl]phenylacetamides", 23, pp. 1102-1108 (1980).

*Primary Examiner*—Richard L. Raymond
*Assistant Examiner*—Mark W. Russell
*Attorney, Agent, or Firm*—Joy Ann Serauskas; Paul D. Matukaitis

[57] ABSTRACT

Compositions of matter are disclosed of compounds of the formula

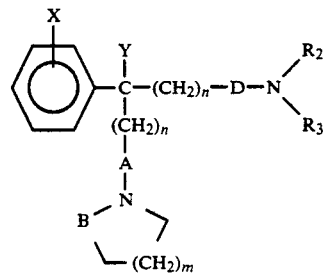

and the pharmaceutically acceptable acid addition salts thereof wherein X represents a halo, lower alkyl, hydrogen, trifluoromethyl, phenyl, or lower alkoxy substituent; Y represents —CN, —CONH$_2$, —CON(R$_1$)$_2$ or —CO$_2$R$_1$ where R$_1$ is a lower alkyl; m is the integer 1 or 2 and n is an integer from 1 to 3 inclusive; R$_2$ represents lower alkyl; R$_3$ represents lower alkyl or acetyl, aroyl, phenacetyl or trifluoroacetyl; A, B, and D are carbonyl or methylene such that when one of A, B, or D is carbonyl, the others are methylene and R$_3$ is lower alkyl, whereas when R$_3$ is acetyl, aroyl, phenacetyl or trifluoroacetyl, A, B, and D are methylene. These compounds have utility as antiarrhythmic agents.

5 Claims, No Drawings

MONOBASIC DISOBUTAMIDE DERIVATIVES

This is a continuation of application Ser. No. 07/286,588, filed Dec. 19, 1988, abandoned, which is a continuation of application Ser. No. 06/889,431, filed Jul. 25, 1986, now abandoned, which is a continuation of application Ser. No. 06/628,933, filed Jul. 9, 1984, now U.S. Pat. No. 4,639,524.

BACKGROUND OF THE INVENTION

1. Field of the Invention

The structure and synthesis of antiarrhythmic compounds of Formula 1.

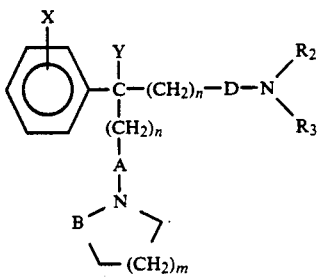

wherein X represents a halo, trifluoromethyl, phenyl, hydrogen, lower alkyl or lower alkoxy substituent; Y represents CN, CONH$_2$, CON(R$_1$)$_2$, CO$_2$R$_1$ where R$_1$ represents lower alkyl; m is the integer 1 or 2 and n is an integer from 1 to 3 inclusive; R$_2$ represents lower alkyl; R$_3$ represents lower alkyl or acetyl, aroyl phenacetyl or trifluoroacetyl; A, B and D are carbonyl or methylene such that when one of A, B, or D is carbonyl the others are methylene and R$_3$ is lower alkyl, whereas when R$_3$ is acetyl, aroyl, phenacetyl or trifluoroacetyl, A, B, and D are methylene.

2. Description of the Prior Art

Compounds of the formula

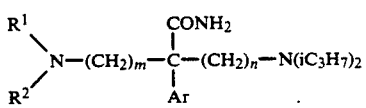

and the non-toxic pharmacologically acceptable acid addition salts thereof; wherein R$^1$ is lower alkyl having from 1 to 7 carbon atoms or along with R$^2$ is cycloalkyl having 5 or 6 carbon atoms; R$^2$ is lower alkyl having from 1 to 7 carbon atoms or along with R$^1$ is cycloalkyl having 5 to 7 carbon atoms; Ar is phenyl, trifluoromethylphenyl or phenyl substituted with 1 or 2 halogens or lower alkyl having from 1 to 4 carbon atoms; and m and n are each integers from 2 to 4 inclusive.

These compounds were disclosed in U.S. Pat. No. 4,107,205 (Renbarger et al.). The compounds of the present invention can be distinguished from the prior art by the absence of a second basic center (tertiary amine) in the molecule.

SUMMARY OF THE INVENTION

A compound of formula 1

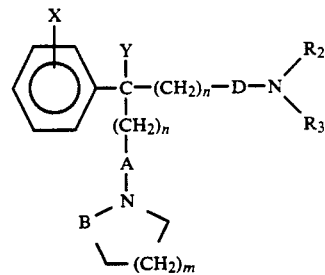

and the pharmaceutically acceptable acid addition salts thereof wherein X represents a halo, trifluoromethyl, phenyl, lower alkyl or lower alkoxy substituent; Y represents CN, CONH$_2$, CON(R$_1$)$_2$, CO$_2$R$_1$ where R$_1$ represents lower alkyl; m is the integer 1 or 2 and n is an integer from 1 to 3 inclusive; R$_2$ represents lower alkyl; R$_3$ represents lower alkyl or acetyl, aroyl phenacetyl or trifluoroacetyl; A, B, and D are carbonyl or methylene such that when one of A, B, or D is carbonyl the others are methylene and R$_3$ is alkyl, whereas when R$_3$ is acetyl, aroyl, phenacetyl or trifluorocetyl, A, B, and D are methylene. These compounds can be distinguished from the prior art by the absence of a second basic center (tertiary amine) in the molecule and this change in structure results in compounds with a more desirable hemodynamic profile.

A preferred embodiment of the invention has a carbonyl at A with B and D methylene and R$_3$ is lower alkyl and Y is CO$_2$R$_1$, CN or CON(R$_1$)$_2$. Still another preferred embodiment of the invention has a carbonyl at B with A and D methylene and R$_3$ is lower alkyl and Y is CO$_2$R$_1$, CN or CON(R$_1$)$_2$. Yet another preferred embodiment of the invention has a carbonyl at D with A and B methylene and R$_3$ is lower alkyl and Y is CO$_2$R$_1$, CN or CON(R$_1$)$_2$.

Another preferred embodiment has methylene at A, B and D and Y is CONH$_2$, CN, CO$_2$R$_1$ or CON(R$_1$)$_2$ wherein R$_1$ is a lower alkyl and R$_3$ is acetyl, aroyl, phenacetyl or trifluoroacetyl.

DETAILED DESCRIPTION OF THE INVENTION

Reaction of the nitrile (II) with 1-(chloroacetyl) piperidine in the presence of sodium hydride provides the corresponding amide (III). The nitrile function may be replaced by an ester or a dimethyl amide function by using the ester or the dimethyl amide analog of (II) as a reactant. The intermediates (II) are broadly described in J. Med. Chem. 23, 1102–1108 (1980).

Reaction of the nitrile (IV) with N-benzyl,N-isopropylaminoethyl chloride in the presence of sodium amide in toluene at 85° C. for 1 hr affords the corresponding nitrile (V). Hydration of the nitrile (V) with sulfuric acid followed by catalytic hydrogenation provides the corresponding amide (VI). Acylation of (VI) with acetyl chloride or other acyl chlorides such as trifluoroacetyl, aroyl or phenacetyl yields the desired acylated amide (VII).

Treatment of the nitrile (IV) with sodium hydride in N,N-dimethylformamide followed by 1-chloro-N,N-bis-(1-methylethyl)acetamide affords the nitrile amide VIII as shown in Scheme III.

Reaction of the nitrile II with lithium diisopropylamide in THF followed by treatment with tris (isopropoxy) titanium chloride [Helv. Chim. Acta., 64, 357

(1981)] and subsequent condensation with N-(2-chloroethyl)pyrrolidin-2-one produces the nitrile-pyrrolidone IX as shown in Scheme IV.
Compounds of this invention are prepared by the following reaction schemes.
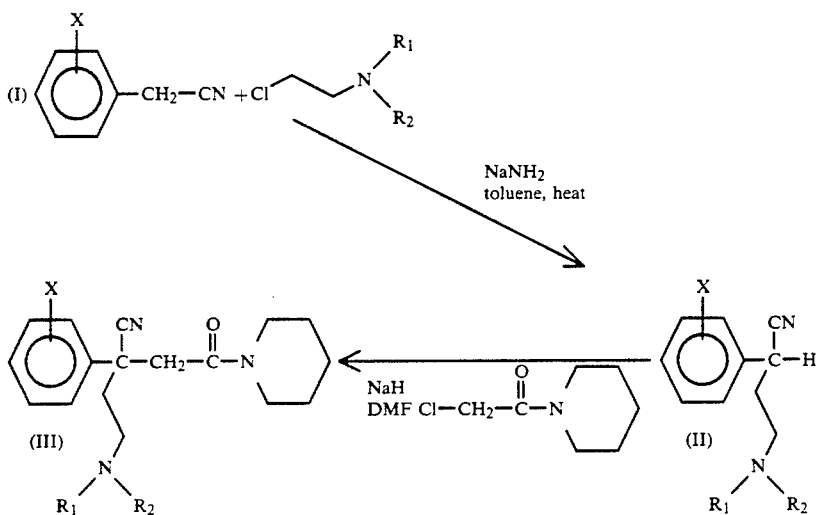
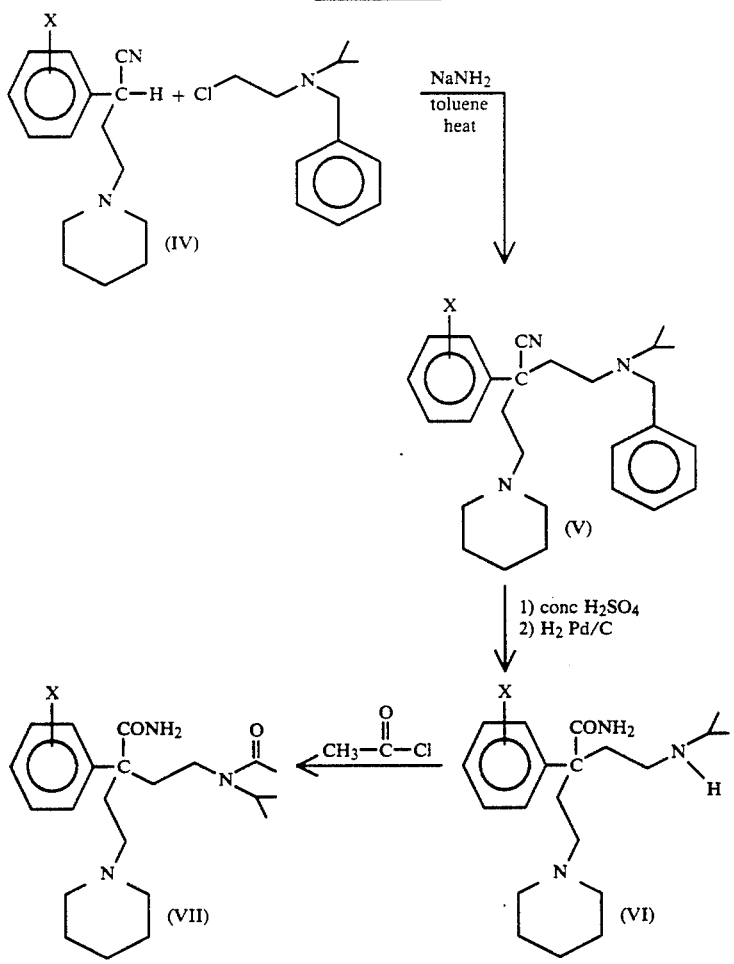

Scheme (III)

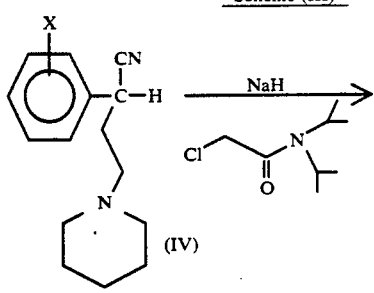

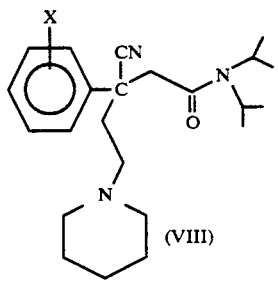

Scheme (IV)

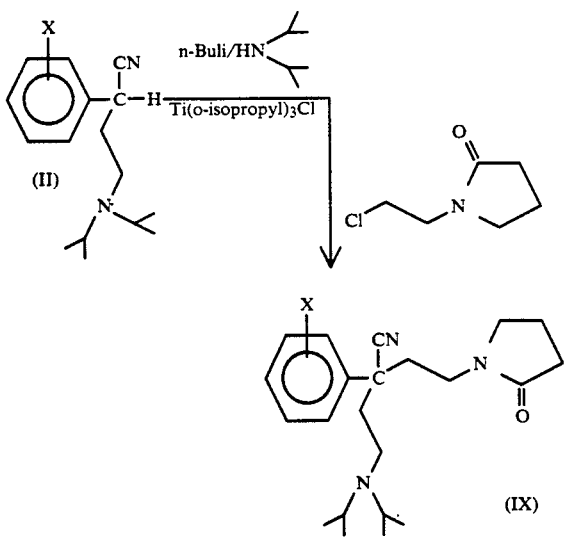

In compounds of formula 1, the term lower alkyl refers to straight or branched chain alkyls having 1 to 6 carbon atoms such as methyl, ethyl, propyl, isopropyl, butyl, pentyl, hexyl and the like. The term lower alkoxy refers to alkoxy groups having 1 to 6 carbon atoms from straight or branched lower alkyls or described above. Thus, methoxy, ethoxy, propoxy, butoxy, and the like are suitable lower alkoxy groups. Halo refers to halogens such as chlorine, bromine, fluorine, and, iodine. Aroyl refers to benzyl and substituted benzoyl chlorides. Phenacetyl refers to an unsubstituted or optionally substituted phenyl group.

Positioning of the substituent X relative to the point of attachment of the phenyl is not critical. Thus, within the scope of this invention are ortho, meta or para monosubstituted phenyls wherein the X represents a halogen, trifluoromethyl, phenyl, lower alkyl or lower alkoxy substituent. A preferred embodiment of this invention, when X is chlorine, is a 2-chloro-substituted phenyl.

Pharmaceutically acceptable acid addition salts are derived from acids such as hydrochloric, hydroiodic, hydrobromic, phosphoric, sulfuric, toluenesulfonic, acetic, maleic, benzoic, and the like.

Compounds of this invention are useful by virtue of their ability to inhibit ventricular arrhythmia as indicated by the following test.

Ventricular arrhythmia is induced by a 2-stage ligation of the anterior descending branch of the left coronary artery in each of two or more unanesthetized dogs. The test compound is administered intravenously at 5 mpk doses to a maximum dose of 20 mpk. A compound is rated active if it produces at least a 25% reduction in ectopic beats for a period of at least 10 minutes in half or more of the dogs tested. The average minimal effective dose is determined for each active compound.

Anti-arrhythmic agents effective in man such as quinidine, procainamide, and Norpace ® are active in this test.

Those compounds found active to the extent of 75-100% reduction in ventricular arrhythmia or toxic in the above test at 5 mpk are tested by administering a 1 mpk dose at five minute intervals. A compound is rated active if it produces at least a 25% reduction in ectopic beats for a period of at least 10 minutes in half or more of the dogs tested.

Table I illustrates the activity of preferred compounds of this invention.

TABLE I

| Compound | Dose (mg/kg) | Result | Length of Duration (Mins.) |
|---|---|---|---|
| Example 1 | 5 | Active | 10.0 |
| Example 3 | 6 | Active | 15.0 |
| Example 5 | 5 | Active | 12.5 |
| Example 6 | 10 | Active | 22.5 |

The compounds of the present invention can be distinguished from those of the prior art by the fact they possess a more desireable hemodynamic profile. Thus, while the compounds of the present invention suppress ventricular arrhythmias in unanesthetized dogs in the same dose range as those compounds of the prior art described in U.S. Pat. No. 4,107,205, they possess diminished myocardial depressant activity as shown Table II. This reduction of negative inotropic action is particularly beneficial in the dysrhythmic heart where suppression of contractility can be particularly life threatening.

TABLE II

| *Example 21 | dp/dt = −42% at MED |
| Example 6 | dp/dt = −20% at MED |
| Example 3 | dp/dt = −23% at MED |
| Example 5 | dp/dt = −28% at MED |

*From U.S. Pat. No. 4,107,205

Compounds of this invention are formulated into conventional dosage forms such as tablets, capsules, and injectibles.

The hereinafter set out examples are intended to illustrate the invention and not limit it in spirit or scope.

DESCRIPTION OF THE PREFERRED EMBODIMENTS

Example 1

Preparation of 1-[5-[bis(1-methylethyl)amino]-3-(2-chlorophenyl)-3-cyano-1-oxopentyl] piperidine 2.0 g of sodium hydride (50% in oil) washed with hexane to remove the oil, is added to a solution of 11.2 g of α-[2-BIS(1-methylethyl)amino]ethyl-2-chloro phenylacetonitrile in 75 ml of N,N-dimethylformamide. The mixture is stirred at room temperature under nitrogen atmosphere for 45 minutes, and then 6.4 g of 1-(chloroacetyl)piperidine is added to the mixture. The reaction mixture is stirred at room temperature for 1 hour, poured into water and extracted with ether. The ether extract is washed with water, dried over magnesium sulfate. The solvent is removed by evaporation under reduced pressure to provide crude product which is crystallized from hexane to provide 9.2 g of 1-[5-[bis(1-methylethyl)amino]-3-(2-chloro phenyl)-3-cyano-1-oxopentyl]piperidine having the formula

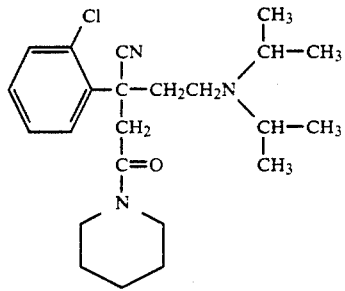

Calcd. for $C_{23}H_{34}N_3OCl$: C, 68.38; H, 8.48; N, 10.40.
Found: C, 68.29; H, 8.45; N, 10.37.
IR (CHCl$_3$) 2230 cm$^{-1}$, 1650 cm$^{-1}$.
M.P 87°–89° C.

EXAMPLE 2

Preparation of methyl α-[2-bis(1-methylethyl)amino)ethyl]-2-chlorobenzeneacetate To a stirred solution of 100 g of α-[2-bis(1-methylethyl)amino]ethyl-2-chlorophenylacetonitrile in 200 ml of methanol is added 100 ml of concentrated sulfuric acid. The reaction mixture is refluxed for 6 hours. After cooling to room temperature, the solution is poured into ice water and this solution is carefully neutralized with 50% sodium hydroxide solution. The basic solution is extracted with 2×300 ml portions of ether and the extracts are washed with water and dried over anhydrous magnesium sulfate. The solvent is removed by evaporation under reduced pressure to provide crude product, which is distilled at [142°–148° C. (0.3 mm)] to provide 85.1 g of methyl α-[2-[bis(1-methylethyl)amino]ethyl]-2-chlorobenzeneacetate having the formula

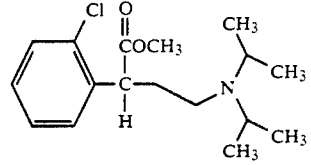

Calcd. for $C_{17}H_{26}ClNO_2$: C, 65.45; H, 8.40; N, 4.49.
Found: C, 65.49; H, 8.46; N, 4.40.
IR (Neat): 1735 cm$^{-1}$.

EXAMPLE 3

Preparation of methyl α-[2-[bis(1-methylethyl)amino]ethyl]-α-(2-chlorophenyl)-γ-oxo-1-piperidinebutanoate 37.5 ml of 1.6M n-butylliithium is added to 8.4 ml of diisopropylamine in 200 ml of freshly distilled THF at 0° C. under nitrogen atmosphere. The mixture is stirred at 0° C. for 30 minutes, cooled to −50° C., and 18.6 g of material prepared in Example 2 in 100 ml of THF is added. The reaction mixture is stirred at −50° C. for 30 minutes before 8.5 g of 1-(chloroacetyl) piperidine is added at −50° C. and then warmed to room temperature where it as kept then for 2 hours. The mixture is poured onto water and extracted with 3×200 ml portions of ether and the extracts are washed with water, dried over anhydrous magnesium sulfate and the solvent is removed under reduced pressure. The resultant crude product is crystallized from hexane to provide methyl α-[2-[bis(1-methylethyl)amino]ethyl]-α-(2-chlorophenyl)-γ-oxo-1-piperidinebutanoate, having the formula

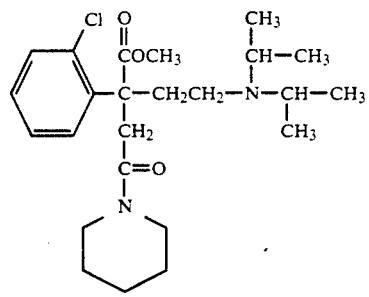

Calcd. for $C_{24}H_{37}N_3O_3Cl$: C, 65.96; H, 8.53; N, 6.41.
Found: C, 65.84; H, 8.51; N, 6.45.
M.P.: 104°–106° C.

EXAMPLE 4

Preparation of N,N-dimethyl-α[2-bis(1-methylethyl)-amino]-ethylphenyl acetamide

To 6.0 g of potassium hydride (35% in oil) in 20 ml of freshly distilled THF under argon atmosphere is added 4.0 g of N, N-dimethylphenylacetamide in 20 ml of THF over 33 minutes by motor driven syringe, and the mixture is stirred at room temperature for 10 minutes. 4.32 g of N,N-diisopropylaminoethyl chloride in 6 ml of THF is added over a 33 minute period, and the mixture is stirred at room temperature for 6 hours. The reaction mixture is then poured onto ice water and extracted with 3×50 ml portions of ether. The ether extract is washed with water, followed by saturated sodium chloride solution and dried over magnesium sulfate. The solvent is removed by evaporation under reduced pressure to provide crude product, which is taken up in 1N hydrochloric acid solution. The acidic solution is washed with pentane before basifying with 50% sodium hydroxide solution and extracting the aqueous solution with 3×50 ml portions of ether. The ether extracts are dried over magnesium sulfate and the solvent is removed under reduced pressure to provide 3.77 g. of N,N-dimethyl-α-[2-bis(1-methylethyl)amino]ethyl-phenyl acetamide having the formula

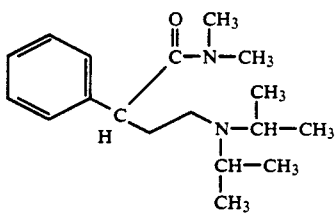

IR (CHCl₃) 2970, 1640 cm⁻¹.
NMR (¹H, δ, CDCl₃, 60 MHz) 7.32 (5H, m, ArH's), 3.85 (1H, m), 2.90 (6H, s, CON(Me)₂).

EXAMPLE 5

Preparation of α-[2-[bis(1-methylethyl)amino]ethyl]-N,N-dimethyl-γ-oxo-α-phenyl-1-piperidinebutanamide Following the procedure described in Example 3 and using the product of Example 4 provides α-[2-[bis(1-methylethyl)amino]ethyl]-N,N-dimethyl-γ-oxo-α-phenyl-1-piperidinebutanamide having formula:

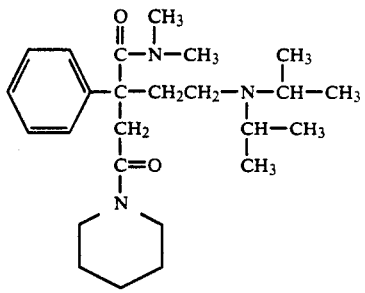

Calcd. for C₂₅H₄₁N₃O₂: C, 72.25; H, 9.94; N, 10.12. Found: C, 72.00; H, 9.87; N, 10.18.
M.P.: 142°–145° C.

EXAMPLE 6

Preparation of α-[2-[acetyl(1-methylethyl)amino]ethyl]-α-(2-chlorophenyl)-1-piperidinebutanamide 1.37 g of acetyl chloride is added to 6.0 g of α-[2-(1-methylethyl)aminoethyl]-α-(2-chlorophenyl)-1-piperidinebutanamide in 100 ml of chloroform and 1.71 g of triethylamine at 0° C. under nitrogen atmosphere. The reaction mixture is stirred at 0° C. for 1 hour, then allowed to warm to room temperature and poured into water. The layers are separated and the organic extract is washed with water and dried over magnesium sulfate. The solvent is removed by evaporation under reduced pressure to provide crude product which is crystallized from ethyl acetate to provide 4.51 g of α-[2-[acetyl(1-methylethyl)amino]ethyl-α-(2-chlorophenyl)-1-piperidinebutanamide having the formula

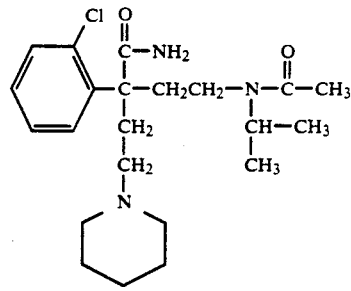

Calcd. for C₂₂H₃₄N₃O₂Cl: C, 64.71; H, 8.40; N, 10.30. Found: C, 65.10; H, 8.36; N, 10.31.
M.P 140°–141° C.

EXAMPLE 7

Preparation of α-[2-[trifluoroacetyl-(1-methylethyl)amino]ethyl]-α-(2-chlorophenyl)-1-piperidinebutanamide Following the procedure in Example 6 and replacing acetylchloride with trifluoroacetic anhydride provides α-[2-[trifluoroacetyl(1-methylethyl)amino]ethyl]-α-(2-chlorophenyl)-1-piperidinebutanamide having formula

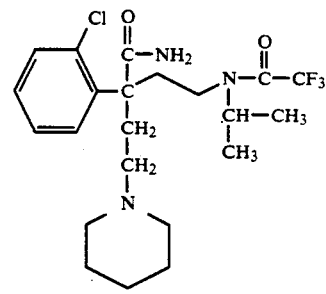

Calcd for C₂₂H₃₁N₃O₂ClF₃: C, 57.19; H, 6.76; N, 9.09. Found: C, 57.10; H, 6.94; N, 8.67.

Example 8

Preparation of β-(2-chlorophenyl)-β-cyano-N,N-bis(1-methylethyl)-1-piperidinepentanamide Following the procedure in Example 1 and replacing α-[2-Bis(1-methylethyl)amino]ethyl-2-chlorophenylacetonitrile with α-(2-chlorophenyl)-1-piperidinebutanenitrile and substituting 1-(chloroacetyl)piperidine with 1-chloro-N,N-bis(1-methylethyl)acetamide provides β-(2-chlorophenyl)-β-cyano-N,N-bis(1-methylethyl)-1-piperidinepentanamide having formula

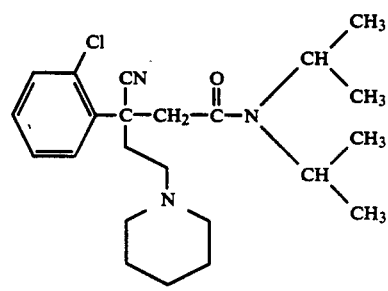

Calcd for C₂₃H₃₄N₃OCl: C, 68.38; H, 8.48; N, 10.40.
Found: C, 68.38; H, 8.46, N, 10.38.
M.P.: 83°–85° C.

Example 9

Preparation of
α-(2-chlorophenyl)-α-{[2-bis(1-methylethyl)amino]ethyl}-2-oxo-1-pyrrolidinebutanenitrile A solution of α-[2-bis(1-methylethyl)amino]ethyl-2-chloroacetonitrile in THF is treated with one equivalent of freshly prepared LDA at −78° C. After ten minutes, one equivalent of 2M tris (isopropoxy) titanium chloride in hexane is added and the reaction mixture is allowed to warm to room temperature. To the reaction mixture is then added one equivalent of 2-chloroethylpyrrolidin-2-one in THF and the solution is stirred for 1 to 6 hours. After pouring the reaction mixture into 2N HCl solution, the aqueous phase is washed with ether before basifying with sodium hydroxide solution. The alkaline solution is extracted three times with ether and the extracts are washed with saturated salt solution and dried (Na₂SO₄). Solvent removal in vacuum gives α-(2-chlorophenyl)-α-{[2-bis(1-methylethyl)amino]ethyl}-2-oxo-1-pyrrolidinebutanenitrile having the formula:

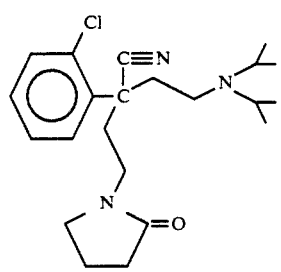

What is claimed is:

1. A compound comprising the following formula

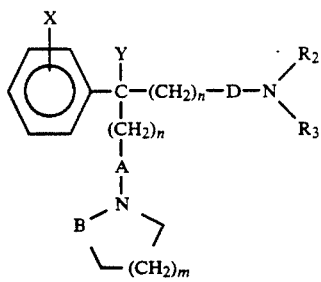

and the pharmaceutically acceptable acid addition salts thereof wherein X represents a halo, lower alkyl, hydrogen, trifluoromethyl, phenyl, or lower alkoxy substituent; Y represents —CN, —CONH₂, CON(R₁)₂ or CO₂R₁ where R₁ is a lower alkyl; m is the integer 2 and n is an integer from 1 to 3 inclusive; R₂ represents lower alkyl; R₃ represents lower alkyl; A is carbonyl; B and D are methylene.

2. A compound comprising the formula

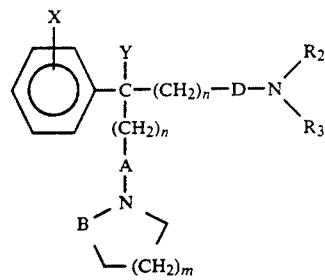

and the pharmaceutically acceptable addition salts thereof wherein X represents halo, lower alkyl, or hydrogen; Y represents —CN, —CONH₂, —COOR₁ or —CON(R₁)₂ where R₁ is a lower alkyl; m is the integer 2 and n is an integer of from 1 to 2 inclusive; R₂ represents lower alkyl; R₃ represents lower alkyl; A is carbonyl, B and D are methylene.

3. A compound as claimed in claim 2, which is of the formula:

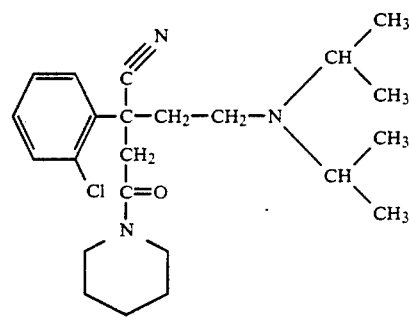

4. A compound as claimed in claim 2, which is of the formula:

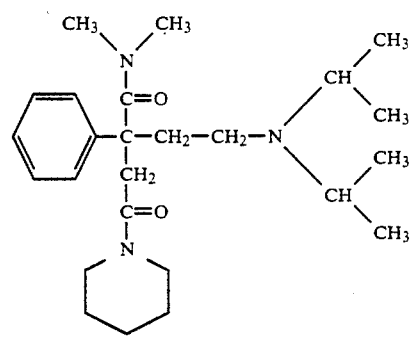

5. A compound as claimed in claim 2, which is of the formula:

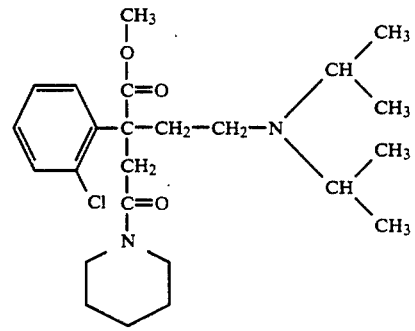

* * * * *

UNITED STATES PATENT AND TRADEMARK OFFICE
CERTIFICATE OF CORRECTION

PATENT NO. : 5,097,035
DATED     : March 17, 1992
INVENTOR(S) : Bipinchandra N. Desai, et al It is certified that error appears in the above-identified patent and that said Letters Patent is hereby corrected as shown below:

Column 2, line 24, reading "trifluorocetyl" should read -- trifluoroacetyl --.

Signed and Sealed this

Twenty-eighth Day of September, 1993

Attest:

BRUCE LEHMAN

*Attesting Officer*    Commissioner of Patents and Trademarks